United States Patent [19]

Kanojia et al.

[11] Patent Number: 4,714,705
[45] Date of Patent: Dec. 22, 1987

[54] 4-NITROGEN SUBSTITUTED ISOQUINOLINOL COMPOUNDS HAVING CARDIOTONIC, PHOSPHODIESTERASE FRACTION III INHIBITING PROPERTIES AND/OR RENAL VASODILATING PROPERTIES

[75] Inventors: Ramesh M. Kanojia, Somerville; Robert Falotico, Belle Mead, both of N.J.; Alfonso J. Tobia, Doylestown, Pa.; Jeffery B. Press, Rocky Hill, N.J.

[73] Assignee: Ortho Pharmaceutical Corporation, Raritan, N.J.

[21] Appl. No.: 882,655

[22] Filed: Jul. 7, 1986

[51] Int. Cl.[4] .................. A61K 31/47; C07D 217/24
[52] U.S. Cl. .................................... 514/309; 546/141
[58] Field of Search ......................... 546/141; 514/309

[56] References Cited

U.S. PATENT DOCUMENTS 4,639,521  1/1987  Sannohe et al. .................... 546/141

Primary Examiner—Glennon H. Hollrah
Assistant Examiner—James H. Turnipseed
Attorney, Agent, or Firm—Benjamin F. Lambert

[57] ABSTRACT

Substituted 3-isoquinolinol compounds of the general formula

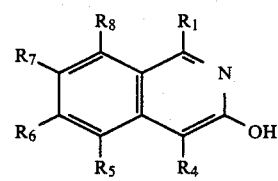

that exhibit cardiotonic and/or phosphodiesterase fraction III inhibiting properties and/or renal vasodilating are pharmacologically active in the treatment of cardiac conditions. Methods for synthesizing and using those compounds are described.

16 Claims, No Drawings

4-NITROGEN SUBSTITUTED ISOQUINOLINOL COMPOUNDS HAVING CARDIOTONIC, PHOSPHODIESTERASE FRACTION III INHIBITING PROPERTIES AND/OR RENAL VASODILATING PROPERTIES

TECHNICAL FIELD

The present invention relates to 3-isoquinolinol compounds that exhibit cardiotonic, phosphodiesterase fraction III inhibiting properties and/or renal vasodilating properties along with methods for synthesizing and using those compounds.

BACKGROUND

Compounds that exhibit cardiotonic properties cause cardiac muscle (in particular, the myocardium) to pump more forcefully and effectively. Cardiotonic agents are often used to treat heart failure because they can relieve one of the early effects of the condition—the buildup of fluid in the body tissues. Blood circulation is also improved.

The administration of a cardiotonic agent provides what is known as a "positive inotropic effect" or an increase in the contractile force of cardiac muscle in a dose-dependent manner. Digitalis is one of the most frequently used cardiotonic agents; other examples include ouabain and strophanthidin.

The administration of vasodilators or vasodilating agents produces a relaxation of the muscles of the blood vessels. This has the effect of enlarging the blood vessel passage, reducing resistance to the flow of blood and lowering the blood pressure. As a result, more blood reaches the tissues. Examples of such agents include nitroglycerin, other nitrates, hydralazine and the like. Renal vasodilators, of course, produce a relaxation of the muscles of blood vessels that are associated with the kidneys.

Phosphodiesterases convert cyclic-AMP (cyclic adenosine monophosphate or "cAMP") to 5'-AMP. Phosphodiesterase fraction III is one example of a biologically active phosphodiesterase. Compounds including theophylline and caffeine inhibit phosphodiesterase activity and its breakdown of cAMP; therefore, a high level of cAMP in the blood is maintained.

Compounds that exhibit cardiotonic and vasodilating properties and which also inhibit the hydrolytic activity of phosphodiesterases would be a substantial improvement over currently available compounds that do not possess each of the foregoing properties.

A number of compounds that are structurally related to isoquinolines and isoquinolinols have been described in the literature.

U.S. Pat. Nos. 3,798,225, 3,910,927 and 4,015,006 to Kreighbaum et al. (Mead Johnson and Co.) relate to 2-substituted-3(2H)-isoquinolones and 2-substituted-3-alkoxyisoquinolines that are reported to have hypotensive and peripheral vasodilating properties upon oral administration. The patents relate in particular to 1-benzyl derivatives of the above compounds.

The preparation of 3-hydroxy-6,7-dimethoxy-1-methylisoquinoline and the corresponding tautomeric form, 6,7-dimethoxy-1-methyl-3(2H)-isoquinolone, which is the parent compound of several compounds of this invention, has been reported along with the preparation of the corresponding 3-ethoxy and 3-acetoxy derivatives. [Bentley et al., *J. Chem Soc.*, 1763 (1952); Dorofeenko et al., *USSR Author's Certificate No.* 207,921, CA, 69, 52003x (1967); and D. Evans et al., *J. Chem Soc.* (B), 590 (1967)].

The compounds used as starting materials in this invention are prepared according to the procedures described in our copending application U.S. Ser. No. 871,967 filed on June 9, 1986 all of said procedures being incorporated herein by reference.

1-Phenylisoquinoline derivatives are described in Ger. Offen. DE 3,227,741 which issued to Hoechst AG. The compounds are reported to exhibit antidepressant activity. U.S. Pat. Nos. 4,282,222 and 4,282,223 to Bartmann et al. (assigned to Hoechst A-G) describe isoquinolines including 3-piperidino, 3-piperazino and 3-piperazino N-substituted derivatives that are reported to exhibit antidepressant activity.

U.S. Pat. No. 3,641,032 to Zinnes et al. (Warner-Lambert Company) describes immunosuppressive compositions that include 2-ethyl-3-hydroxy-1(2H)-isoquinolone diphenylcarbamate.

U.S. Pat. No. 3,870,721 to Archibald et al. relates to 4-alkanoylamino isoquinolinediones and 3-alkanoyloxy-4-alkanoylamino isoquinolones. A representative isoquinolinedione which is reported to inhibit blood platelet aggregation is 4-acetamido-1,2,3,4-tetrahydro-1,3-isoquinolinedione.

U.S. Pat. No. 3,954,771 to Geerts et al., which patent is assigned to UCB Society Anonyme, describes a process for the preparation of 2H-3-isoquinolones. The foregoing compounds are described as precursors for the synthesis of 1,4-dihydro-1,4-ethanoisoquinoline-3(2H)ones (described in U.S. Pat. No. 3,781,436) that are reported to be active in the central nervous system (CNS-active) for the treatment of disorders including insomnia and vertigo.

U.S. Pat. No. 4,041,077 to Ghosez et al. (UCB Societe Anonyme) describes the use of N-benzyl-2,2-dimethoxyacetamides in the synthesis of 2H-3-isoquinolones which, in turn, may be used in the synthesis of 1,4-dihydro-1,4-ethano-isoquinolin-3(2H)ones.

DETAILED DESCRIPTION OF THE INVENTION

3-Isoquinolinols, pharmaceutical compositions containing a 3-isoquinolinol compound as an active ingredient, methods of treating a mammal exhibiting a cardiac condition and methods for synthesizing the present compounds are contemplated. The terms "3-isoquinolinol", "isoquinolinol" and grammatical forms thereof are used herein to indicate the useful compounds of the present invention.

In particular, the invention contemplates a 3-isoquinolinol having a structure that corresponds to the formula I:

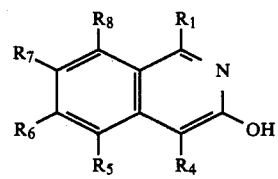

wherein
$R_1$ is a radical selected from the group consisting of hydrogen, lower alkyl, aryl and halogen-substituted radicals thereof;

$R_4$ is a radical selected from the group consisting of nitro, nitroso, amino, disubstituted amino wherein the substituent is lower alkyl having 1–5 carbon atoms and radicals of the formula $NHCO(Y)(R)_n$ wherein Y is oxygen or $N(H)_x$ and R is hydrogen, lower alkyl, cycloalkyl, aryl, lower alkenyl or lower alkynyl having 3–5 carbon atoms, lower alkoxy or aralkyl, and n and x are independently 0, 1 or 2, with the proviso that if Y is oxygen, R is other than hydrogen and n is 1, and when n is 2, x is 0; and $R_5$, $R_6$, $R_7$ and $R_8$ may be independently selected from the group consisting of hydrogen, halogen, hydroxy, and lower alkoxy; and $R_5$ and $R_6$, $R_6$ and $R_7$ or $R_7$ and $R_8$ when taken together may be methylenedioxy.

3-Isoquinolinol compounds that contain a substituent $R_4$ (as defined herein), in any combination with substituents $R_1$, $R_3$, $R_5$ through $R_8$ (as further defined herein and present either singly or in combination) have not been previously reported. The compounds having structures that correspond to the foregoing formula are also capable of existing as the corresponding 3-keto tautomeric forms.

Also contemplated are pharmaceutically acceptable salts of a compound of this invention. Any conventional pharmaceutically acceptable salt can be used. Among the salts that can be prepared are alkali metal salts including lithium, sodium and potassium; alkaline earth metal salts including calcium and magnesium; and aluminum, zinc and iron.

Also contemplated are the hydrohalide salts of the isoquinolinols of this invention, such as the hydrobromide and hydrochloride salts as well as the salts of other mineral acids such as the sulfates and the phosphates.

Exemplary compounds of the present invention whose structures conform to the above formula are listed in Table 1, below.

TABLE 1

3-Isoquinolinol Derivatives

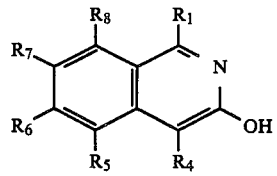

| Compound | Prepared According To Example | $R_1$ | $R_4$ | $R_5$ | $R_6$ | $R_7$ | $R_8$ | Melting Point °C. |
|---|---|---|---|---|---|---|---|---|
| BA | 1 | $CH_3$ | $NO_2$ | H | $OCH_3$ | $OCH_3$ | H | >300 |
| BB | 1 | $CH_3$ | $NO_2$ | H | O—$CH_2$—O | | H | >300(d) |
| BC | 1 | H | $NO_2$ | H | O—$CH_2$—O | | H | >300(d) |
| BD | 1 | $CH_3$ | $NO_2$ | $NO_2$ | $OCH_3$ | $OCH_3$ | $OCH_3$ | 225(d) |
| BE | 1 | $CH_3$ | $NO_2$ | H | $OCH_3$ | $OCH_3$ | $OCH_3$ | 250–252 |
| BF | 3 | H | $NHCOCH_3$ | H | $OCH_3$ | $OCH_3$ | H | 284–286 |
| BG | 3 | $CH_3$ | $NHCOCH_3$ | H | $OCH_3$ | $OCH_3$ | H | >300(d) |
| BH | 1 | $CH_3$ | $NO_2$ | H | $OCH_3$ | $OC_2H_5$ | H | 257–260(d) |
| BI | 1 | $CH_3$ | $NO_2$ | H | $OCH_3$ | $OC_4H_{9n}$ | H | 210(d) no melt |
| BJ | 3 | $CH_3$ | $NHCOCH_3$ | H | $OCH_3$ | $OC_2H_5$ | H | 293–294(d) |
| BK | 1 | $CH_3$ | $NO_2$ | H | $OC_2H_5$ | $OC_2H_5$ | H | 240–243(d) |
| BL | 1 | $C_6H_5$ | $NO_2$ | H | $OCH_3$ | $OCH_3$ | H | 248–250 |
| BM | 5 | $CH_3$ | $NHCONH_2$ | H | $OCH_3$ | $OCH_3$ | H | 250–255 |
| BN | 3 | $CH_3$ | $NHCO(CH_2)_3CH_3$ | H | $OCH_3$ | $OCH_3$ | H | 215–217(d) |
| BO | 4 | $CH_3$ | $NHCOCH(CH_3)_2$ | H | $OCH_3$ | $OCH_3$ | H | 292–294(d) |
| BP | 6 | $CH_3$ | $NHCONHC_6H_4$—p-$OCH_3$ | H | $OCH_3$ | $OCH_3$ | H | 229–232(d) |
| BQ | 1 | $CH_3$ | $NO_2$ | H | H | $OCH_3$ | H | >250 |
| BR | 6 | $CH_3$ | $NHCONH(CH_2)_3CH_3$ | H | $OCH_3$ | $OCH_3$ | H | 230–232(d) |
| BS | 5 | $CH_3$ | $NHCONH_2$ | H | $OCH_3$ | $OC_2H_5$ | H | >300 |
| BT | 6 | $CH_3$ | $NHCONHC_6H_4$—p-$OCH_3$ | H | $OCH_3$ | $OC_2H_5$ | H | 237–240(d) |
| BU | 6 | $CH_3$ | $NHCONHC_6H_4$—m-$OCH_3$ | H | $OCH_3$ | $OC_2H_5$ | H | 232–233(d) |
| BV | 6 | $CH_3$ | $NHCONH$—$C_6H_4$—p-$CF_3$ | H | $OCH_3$ | $OC_2H_5$ | H | 232–233(d) |
| BW | 6 | $CH_3$ | $NHCONH$—$C_6H_4$—p-Cl | H | $OCH_3$ | $OC_2H_5$ | H | 236–239(d) |
| BX | 6 | $CH_3$ | $NHCONH$—$C_6H_4$—m-Cl | H | $OCH_3$ | $OC_2H_5$ | H | 235–237(d) |
| BY | 6 | $CH_3$ | $NHCONH$—$C_6H_4$—m-$CF_3$ | H | $OCH_3$ | $OC_2H_5$ | H | 232–235(d) |
| BZ | 6 | $CH_3$ | $NHCONH$—$C_6H_4$—p-$CF_3$ | H | $OCH_3$ | $OCH_3$ | $OCH_3$ | 212–214(d) |
| BAA | 6 | $CH_3$ | $NHCONH$—$C_6H_4$—p-Cl | H | $OCH_3$ | $OCH_3$ | $OCH_3$ | 215–217(d) |
| BAB | 6 | $CH_3$ | $NHCONH$—$C_6H_2$—3,4,5-$(OCH_3)_3$ | | $OCH_3$ | $OCH_3$ | $OCH_3$ | 215–217(d) |
| BAC | 6 | $CH_3$ | $NHCONH$—$C_6H_4$—p-F | H | $OCH_3$ | $OCH_3$ | $OCH_3$ | 223–225(d) |
| BAD | 6 | $CH_3$ | $NHCONH$—$C_6H_4$—p-$CF_3$ | H | $OCH_3$ | $OCH_3$ | H | 242–244(d) |
| BAE | 6 | $CH_3$ | $NHCONH$—$C_6H_4$—m-$OCH_3$ | H | $OCH_3$ | $OCH_3$ | H | 239–241(d) |
| BAF | 6 | $CH_3$ | $NHCONHC_6H_4$—m-Cl | H | $OCH_3$ | $OCH_3$ | H | 235–237(d) |
| BAG | 6 | $CH_3$ | $NHCONHC_6H_4$—m-$CF_3$ | H | $OCH_3$ | $OCH_3$ | H | 257–259(d) |
| BAH | 6 | $CH_3$ | $NHCONHC_6H_2$—3,4,5-$(OCH_3)_3$ | H | $OCH_3$ | $OCH_3$ | H | 238–240(d) |
| BAI | 6 | $CH_3$ | $NHCONH$—$C_6H_4$—p-F | H | $OCH_3$ | $OCH_3$ | H | 256–258(d) |
| BAJ | 6 | $CH_3$ | $NHCONHCH_2C_6H_5$ | H | $OCH_3$ | $OC_2H_5$ | H | 230–235(d) |
| BAK | 6 | $CH_3$ | $NHCONH$—$C_6H_4$—p-$NO_2$ | H | $OCH_3$ | $OC_2H_5$ | H | 232–233(d) |
| BAL | 6 | $CH_3$ | $NHCONH$—$C_6H_2$—3,4,5-$(OCH_3)_3$ | H | $OCH_3$ | $OC_2H_5$ | H | 224–225(d) |
| BAM | 6 | $CH_3$ | $NHCONH$—$C_6H_3$—2,4-$(OCH_3)_2$ | H | $OCH_3$ | $OC_2H_5$ | H | 225–228(d) |
| BAN | 1 | $CH_3$ | $NO_2$ | H | $OC_2H_5$ | $OCH_3$ | H | >300(d) |
| BAO | 6 | $CH_3$ | $NHCONHCH_2$—CH=$CH_2$ | H | $OCH_3$ | $OCH_3$ | H | 224–226(d) |
| BAP | 6 | $CH_3$ | $NHCONH$—$C_6H_3$—2,4-$(OCH_3)_2$ | H | $OCH_3$ | $OCH_3$ | H | 248–250(d) |
| BAQ | 6 | $CH_3$ | $NHCONH$—$C_6H_3$—3,5-$(OCH_3)_2$ | H | $OCH_3$ | $OCH_3$ | H | 210–212(d) |
| BAR | 6 | $CH_3$ | $NHCONH$—$C_6H_5$—p-$NO_2$ | H | $OCH_3$ | $OCH_3$ | H | 270–272(d) |
| BAS | 6 | $CH_3$ | $NHCONHCH_2C_6H_5$ | H | $OCH_3$ | $OCH_3$ | H | 248–250(d) |

TABLE 1-continued
3-Isoquinolinol Derivatives

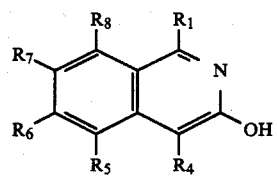

| Compound | Prepared According To Example | R₁ | R₄ | R₅ | R₆ | R₇ | R₈ | Melting Point °C. |
|---|---|---|---|---|---|---|---|---|
| BAT | 6 | CH₃ | NCONH—C(CH₃)=C(CH₃)—O—N (isoxazole) | H | OCH₃ | OCH₃ | H | 258–260(d) |
| BAU | 6 | CH₃ | NCONHC(CH₃)₃ | H | OCH₃ | OCH₃ | H | 276–278(d) |
| BAV | 6 | CH₃ | NCONH—C₆H₄—p-OCH₃ | H | OC₂H₅ | OCH₃ | H | 230–233(d) |
| BAW | 6 | CH₃ | NCONH—C₆H₄—p-CF₃ | H | OC₂H₅ | OCH₃ | H | 245–246(d) |
| BAX | 6 | CH₃ | NHCONH—C(CH₃)=C(CH₃)—O—N (isoxazole) | H | OC₂H₅ | OCH₃ | H | 252–253(d) |
| BAY | 6 | CH₃ | NHCONHCH₂CH₂Cl | H | OCH₃ | OCH₃ | H | 220–222(d) |
| BAZ | 6 | CH₃ | NHCONHCH₂CH₂Cl | H | OC₂H₅ | OCH₃ | H | 210–212(d) |
| BBA | 6 | CH₃ | NHCONH—C₆H₄—p-SCH₃ | H | OC₂H₅ | OCH₃ | H | 223–225(d) |
| BBB | 6 | CH₃ | NHCONH—C₆H₄—m-SCH₃ | H | OC₂H₅ | OCH₃ | H | 214–216(d) |
| BBC | 6 | CH₃ | NHCONH—C₆H₄—p-CO₂C₂H₅ | H | OCH₃ | OCH₃ | H | 222–224(d) |
| BBD | 6 | H | NHCONH—C₆H₄—p-SCH₃ | H | OCH₃ | OCH₃ | H | 254–256(d) |
| BBE | 6 | CH₃ | NHCONH—c-C₆H₁₁ | H | OCH₃ | OCH₃ | H | 248–250(d) |
| BBF | 6 | CH₃ | NHCONH(CH₂)₇CH₃ | H | OCH₃ | OCH₃ | H | 228–230(d) |
| BBG | 6 | H | NHCONH—C₆H₄—p-OCH₃ | H | OCH₃ | OCH₃ | H | 233–235(d) |
| BBH | 6 | CH₃ | NHCONH—C₆H₄—o-OCH₃ | H | OCH₃ | OC₂H₅ | H | 225–230(d) |
| BBI | 6 | CH₃ | NHCONH—C₆H₄—p-SCH₃ | H | OCH₃ | OCH₃ | H | 244–246(d) |
| BBJ | 6 | CH₃ | NHCONH—C₆H₄—m-SCH₃ | H | OCH₃ | OCH₃ | H | 228–230(d) |
| BBK | 6 | CH₃ | NHCONH—C₆H₃—3,5-(CO₂CH₃)₂ | H | OCH₃ | OCH₃ | H | 250–252(d) |
| BBL | 6 | CH₃ | NHCONH—C₆H₃—3,4-(OCH₃)₂ | H | OCH₃ | OCH₃ | H | 243–245(d) |
| BBM | 6 | CH₃ | NHCONH(CH₂)₂Ph | H | OCH₃ | OCH₃ | H | 255–257(d) |
| BBN | 6 | CH₃ | NHCONH(CH₂)₃CH₃ | H | H | OCH₃ | H | 217–220(d) |
| BBO | 6 | CH₃ | NHCONHCH₂CO₂C₂H₅ | H | OCH₃ | OCH₃ | H | 231–233(d) |
| BBP | 7 | CH₃ | NHCO₂(CH₂)₃CH₃ | H | OCH₃ | OCH₃ | H | 282–284(d) |
| BBQ | 2 | CH₃ | NH₂ | H | OCH₃ | OCH₃ | H | 250–253(d) |
| BBR | 7 | CH₃ | NHCO₂CH₃ | H | OCH₃ | OCH₃ | H | 262–264(d) |
| BBS | 6 | CH₃ | NHCONH—C₆H₄—p-OCH₃ | H | H | OCH₃ | H | 197–200(d) |
| BBT | 6 | CH₃ | NHCONH—C₆H₅ | H | OCH₃ | OCH₃ | H | 236–238(d) |
| BBU | 7 | CH₃ | NHCO₂CH(CH₃)₂ | H | OCH₃ | OCH₃ | H | 283–285(d) |
| BBV | 6 | CH₃ | NHCONH—C₆H₄—p-CF₃ | H | H | OCH₃ | H | 265–267 |
| BBW | 6 | CH₃ | NHCONH—(CH₂)₃—Cl | H | OCH₃ | OCH₃ | H | 217–219(d) |
| BBX | 6 | CH₃ | NHCONH—C₆H₄—p-CN | H | OCH₃ | OCH₃ | H | 260–262(d) |
| BBY | 6 | CH₃ | NHCONH—CH₃ | H | OCH₃ | OCH₃ | H | 265–267(d) |
| BBZ | 2 | CH₃ | NHCONH—C₆H₄—p-NH₂ | H | OCH₃ | OCH₃ | H | >300(d) |
| BCA | 8 | CH₃ | NHCONH—C₆H₄—p-COOH | H | OCH₃ | OCH₃ | H | 244–246(d) |
| BCB | 9 | CH₃ | NHCONH—C₆H₄—p-SOCH₃ | H | OCH₃ | OCH₃ | H | 220–222(d) |
| BCC | 7 | CH₃ | NHCO₂CH₂CH=CH₂ | H | OCH₃ | OCH₃ | H | 252–254(d) |
| BCD | 6 | CH₃ | NHCONH—C₂H₅ | H | OCH₃ | OCH₃ | H | 236–238(d) |
| BCE | 6 | CH₃ | NHCONHCH(CH₃)₂ | H | OCH₃ | OCH₃ | H | 237–239(d) |
| BCF | 6 | CH₃ | NO₂ | H | H | OCH₃ | OCH₃ | 214–216 |
| BCG | 8 | CH₃ | NHCONHCH₂CO₂H | H | OCH₃ | OCH₃ | H | 222–224(d) |
| BCH | 6 | CH₃ | NHCONHCO₂CH₃ | H | OCH₃ | OCH₃ | H | 250–252(d) |

(d) = with decomposition.
p = para-substituted.
m = meta-substituted.

As used herein, the term "lower alkyl", in its various uses, indicates a branched or straight chain hydrocarbon having 1 to about 8 carbon atoms, and particularly 1 to about 4 carbon atoms. Lower alkyl radicals include, for example, methyl, ethyl, propyl, isopropyl, n-butyl, sec-butyl, t-butyl, n-pentyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1-octyl, 2-octyl and the like. The term "cycloalkyl" indicates a cyclic alkyl group having 3–6 carbon atoms.

The term "lower alkenyl" indicates a branched or straight chain hydrocarbon having 3–5 carbon atoms such as 2-butenyl, 3-butenyl, allyl and isopentenyl, for example.

The term "aryl", as used herein alone or in combination with other terms, indicates aromatic hydrocarbon groups, such as a phenyl or naphthyl group, which can be unsubstituted or substituted with one or more lower alkyl radicals, halo lower alkyl radicals, hydroxy, lower alkoxy, lower alkylthio, halogens selected from chloro, bromo, iodo and fluoro, CN, $NO_2$, $NH_2$, $SO_2H$, COZ wherein Z is OR or NR'R" wherein R' is hydrogen or lower alkyl and R and R" are hydrogen, lower alkyl, aminolower alkyl, lower alkylaminolower alkyl and lower dialkylaminolower alkyl.

The term "aralkyl" indicates a radical containing a lower alkyl group substituted with an "aryl" radical or substituted aryl radical as defined above.

The phrase "halogen-substituted radical" indicates a lower alkyl or aryl group (in the case of $R_1$) and a lower alkyl, aryl or lower alkoxy-substituted aryl (in the case of R at position $C_4$) that includes a halogen selected from chloro, bromo, iodo and fluoro.

The term "lower alkoxy" indicates a radical containing a lower alkyl group (as defined above) and a terminal oxygen bonded to one or more carbon atom of the isoquinoline ring (at positions $C_5$-$C_8$, inclusive, or in R at position $C_4$). Examples include methoxy, ethoxy, isopropoxy, isopropoxy, n-butoxy, 2-methylpentoxy and the like, with lower alkoxy having 1 to about 4 carbon atoms being particularly preferred.

In particularly preferred practice, $R_1$ is lower alkyl or halogen-substituted lower alkyl, most preferably $C_1$-$C_4$ lower alkyl and halogen-substituted $C_1$-$C_4$ lower alkyl, $R_4$ is nitro or a radical of the formula $NHCO(NH)_xR$ wherein x is zero or 1 and R is selected from hydrogen, lower alkyl, lower alkenyl, aryl, lower alkoxyaryl, nitroaryl, carboxyaryl and haloloweralkylaryl, $R_5$-$R_8$ are hydrogen or alkoxy wherein at least one is alkoxy and preferably where $R_6$ and $R_7$ are both alkoxy or together are methylenedioxy.

In an additional preferred embodiment, $R_1$ is methyl, $R_4$ is nitro or NHCONHR and R is lower alkyl or aryl, $R_5$ is hydrogen, $R_6$ and $R_7$ are methoxy or ethoxy and $R_8$ is hydrogen.

A pharmaceutical composition that comprises an effective amount of an above-described 3-isoquinolinol dispersed in a pharmaceutically acceptable carrier is also contemplated herein. The composition comprises a unit dosage of the isoquinolinol.

The isoquinolinols of this invention have cardiotonic and/or renal vasodilating properties and/or are capable of inhibiting the hydrolytic activity of phosphodiesterase fraction III. In preferred practice, the isoquinolinol of the pharmaceutical composition is capable of producing the desired cardiostimulating and vasodilating effects and inhibiting the hydrolytic activity of phosphodiesterase fraction III in the amount at which that isoquinolinol is present in the pharmaceutical composition, when that composition is introduced as a unit dose into an appropriate mammal such as a laboratory rat.

The term "unit dosage" and its grammatical equivalents are used herein to refer to physically discrete units suitable for administration to human patients and to warm-blooded mammals. Each unit contains a predetermined effective amount of the active ingredient calculated to produce the desired cardiostimulating, vasodilating and phosphodiesterase inhibiting effect in association with the required physiologically tolerable carrier, e.g., a diluent or a vehicle.

The specification for the novel unit dosage forms of this invention are dictated by and are directly dependent on (a) the unique characteristics of the active ingredient, and (b) the limitations inherent in the art of compounding such an active ingredient for therapeutic use in humans and other mammals. Examples of suitable unit dosage forms in accord with this invention are tablets, capsules, pills, powder packets, granules, wafers, and the like, segregated multiples of any of the foregoing, along with liquid solutions, liquid suspensions, elixirs and aerosol suspensions.

The active ingredient is referred to herein as being dispersed in the carrier. Thus, the dispersion formed can be a simple admixture, a non-settling dispersion as in the case of certain emulsions or as an ultimate dispersion, a true solution. In such compositions, the active ingredient is ordinarily present in an amount of at least about 0.5 percent by weight based on the total weight of the composition to about 90 percent by weight.

The effective amount of active ingredient that is administered in vivo depends on the age and weight of the mammal treated, the particular condition to be treated, the frequency of administration, and the route of administration. Exemplary unit doses can contain about 0.01 to about 50 milligrams per kilogram of body weight, more preferably about 0.1 to about 10 milligrams per kilogram of body weight per day and most preferably about 0.1 to about 5 milligrams per kilogram of body weight per day. The human adult dose is typically in the range of about 100 to about 500 milligrams daily, given as a single dose or in 3 or 4 divided doses. Veterinary dosages correspond to human dosages with the amounts administered being in proportion to the weight of the animal as compared to adult humans.

Unit doses containing about 1 to about 50 milligrams of a 3-isoquinolinol per kilogram of laboratory rat body weight (e.g., about 200 grams each) are useful in increasing the force of cardiac contractions.

However, it will be understood that the amount administered is determined by the physician or veterinarian in light of the relevant circumstances including the condition to be treated, the compound to be administered and the route of administration. Therefore, the foregoing dosage ranges are not intended to limit the scope of this invention in any way.

Pharmaceutically acceptable carriers are those well known in the art.

Liquid compositions include liquid phases in addition to or with the exclusion of water. Exemplary of such liquid phases are glycerin and vegetable oils including peanut oil and cottonseed oil.

Suitable solid carriers (diluents) include those materials usually used in the manufacture of pills, capsules or tablets, and include corn starch, lactose, dicalcium phosphate, thickeners such as tragacanth and methylcellulose U.S.P., finely divided silica, polyvinylpyrrolidone, magnesium stearate and the like. Antioxidants such as methylparaben and propylparaben can be present in both solid and liquid compositions, as can sweeteners such as cane sugar, beet sugar, sodium saccharin, sodium cyclamate and the dipeptide methyl ester sweetener sold under the trademark NUTRASWEET (aspartame) by G. D. Searle Co., Skokie, IL.

Methods for stimulating cardiac contractions and for increasing the contractile force of cardiac muscle in a mammal are also contemplated. The methods comprise administering to that mammal a unit dose of a pharmaceutical composition that includes an effective amount of an active ingredient that is an aforementioned 3-isoquinolinol dispersed in a pharmaceutically acceptable carrier. The pharmaceutical composition is preferably maintained within the mammal until the isoquinolinol is cleared from the body of the mammal by natural means such as metabolism or excretion.

The pharmaceutical composition can be administered orally, by injection, by inhalation (for example, in the form of an aerosol, micropulverized powder or nebulized solution) or by any other means well known in the art. In preferred practice, the composition is administered orally as a tablet, capsule or aqueous dispersion.

Inasmuch as a pharmaceutical composition can be administered 3 or more times daily (during a 24 hour period), the methods of increasing the efficiency of cardiac contractions, of increasing the contractile force of cardiac muscle and of stimulating vasodilation can include the serial administration of the pharmaceutical composition into the treated mammal over a given time period; for example, weeks, months or years. In preferred practice, the pharmaceutical composition is administered to the mammal a number of times over a period of about thirty days.

Methods for synthesizing the particular 3-isoquinolinol compounds of this invention are other aspects of the present invention.

The Examples included herein illustrate the preparation of a number of isoquinolinol compounds according to the present invention. By way of summary, the preferred compounds of this invention may be prepared in the following manner.

Methods of Preparation

3-Isoquinolinol compounds of this invention can be prepared by one of the following general methods.

3-Isoquinolinol compounds I wherein $R_4$ is nitro or nitroso can be prepared by electrophilic substitution at $C_4$ of Formula I (wherein $R_4$ is H). In particular, treatment of Compound I with fuming nitric acid in acetic acid, acetic anhydride and the like alone or in combination with ether, methylene chloride and the like provides the 4-nitro derivative; and treatment with $HNO_2$ [generated by combining sodium nitrite and an acid or an alkylnitrite and an acid or base] provides the 4-nitroso derivative.

The 4-nitro or 4-nitroso derivative I can be reduced, for example, by hydrogenation to obtain the 4-amino derivative I (wherein $R_4$ is $NH_2$). If the hydrogenation is performed in the presence of an acid (such as acetic acid) and its anhydride (acetic anhydride), the corresponding 4-N-acylated derivative I (wherein $R_4$ is NHCOR) is provided.

Alternatively, the 4-amino derivative I (wherein $R_4$ is $NH_2$) can be treated with an acid chloride or an anhydride to provide 4-acylamino derivatives I (wherein $R_4$ is NHCOR and R is lower alkyl or aryl); with an inorganic cyanate (for example, NaOCN) in acidic medium (acetic acid) to provide the corresponding urea I (wherein $R_4$ is $NHCONH_2$); with an organic isocyanate to provide a substituted urea I (wherein $R_4$ is NHCONHR and R is lower alkyl or aryl); with an N,N-disubstituted carbamoyl chloride to provide an N,N-disubstituted urea I (wherein $R_4$ is $NHCON(R)_2$ and R is lower alkyl or aryl); or with a chloroformate to provide a carbamate I (wherein $R_4$ is NHCOOR and R is lower alkyl or aryl).

A list of compounds that correspond to the foregoing formulae, their biological activities and experimental procedures for their preparation are included in the following discussion.

A series of 3-isoquinolinols that were synthesized according to the various methods of the present invention are listed in Table 1, hereinbefore.

Having generally described the invention, a more complete understanding can be obtained by reference to the following Examples, which are included for illustrative purposes only and are not intended to be limiting.

BEST MODES OF CARRYING OUT THE INVENTION

In the following Examples, melting points (mp) were determined on a Thomas-Hoover apparatus, and the melting points reported herein are uncorrected. The infrared (IR) spectra were recorded on a Beckman Instruments IR-8 spectrophotometer and are expressed in $cm^{-1}$. Nuclear magnetic resonance (NMR) spectra for hydrogen atoms were obtained in the indicated solvent with tetramethylsilane (TMS) as the internal standard on a Varian T-60A or an IBM WP-100 spectrometer. The values are expressed in $\delta$ units downfield from TMS. Parenthesized, underlined hydrogens were assigned to the resonance positions immediately before the parentheses. Mass spectra were obtained on a Finnigan 1015D quadrupole mass spectrometer coupled to a Finnigan 9500 gas chromatograph or on a Finnigan MAT 8230 Double Focusing high resolution mass spectrometer.

EXAMPLE 1

3-Hydroxy-6,7-dimethoxy-1-methyl-4-nitroisoquinoline (Compound BA)

3-Hydroxy-6,7-dimethoxy-1-methylisoquinoline (0.927 grams, 4.23 mmol) was dissolved in 60 ml glacial acetic acid by warming, and when the solution cooled to 15° C., a crystalline solid separated. To this mechanically stirred slurry were added 1.5 ml of a nitrating mixture (comprising 0.6 ml glacial acetic acid and 0.9 ml of 90 percent nitric acid) over a period of 15 minutes at 15° C. From the reaction mixture, a heavy yellow solid was isolated by filtration and washed with acetic acid. Alternatively, the reaction mixture was first quenched with 300 ml of water and the yellow solid was isolated by filtration, washed with water and dried in vacuo at 50° C. to provide 0.70 grams of Compound 1 (62.7% yield) having a melting point greater than 300° C.

$^1$H NMR (TFA): $\delta$ 3.23 (singlet, 3H, 1-CH$_3$); $\delta$ 4.20 (singlet, 3H, OCH$_3$); $\delta$ 4.32 (singlet, 3H, OC$\underline{H}_3$); $\delta$ 7.65 (singlet, 1H, Ar$\underline{H}$); $\delta$ 8.70 (singlet, 1H, Ar$\underline{H}$).

Mass spectrum: m/e 264 (M+).

Anal. Calculated for $C_{12}H_{12}N_2O_5$: C, 54.55; H, 4.58; N, 10.60. Found: C, 54.24; H, 4.65; N, 10.32.

EXAMPLE 2

4-Amino-3-hydroxy-6,7-dimethoxy-1-methylisoquinoline (Compound BBQ)

3-Hydroxy-6,7-dimethoxy-1-methyl-4-nitroisoquinoline (BA) (16.0 grams, 60.54 mmol) was slurried in 600 ml glacial acetic acid and hydrogenated over 1.5 grams of a 10% palladium on carbon catalyst (Pd/C) at 17 psi hydrogen pressure at room temperature in a Parr hydrogenator for 1.5 hours. The reaction mixture was filtered through a Celite pad, and the filtrate was evaporated to dryness in vacuo to provide 20.48 grams of the diacetate solvate of the title compound as a dark greenish-yellow solid (95.6% yield) having a melting point of 111°–115° C.

$^1$H NMR (CDCl$_3$): δ 2.07 (singlet, 6H, CH$_3$COOH; δ 2.63 (singlet, 3H, 1-CH$_3$); δ 3.90 (singlet, 3H, OCH$_3$); δ 3.95 (singlet, 3H, OCH$_3$); δ 6.57 (singlet, 1H, ArH); δ 6.67 (singlet, 1H, ArH); δ 9.18 (broad singlet, 5H, NH$_2$, OH and CH$_3$COOH).

Mass spectrum: m/e 234 (M+ of free base).

To obtain the free base, the diacetate solvate (3.9 grams, 13.3 mmol) was treated with methanolic sodium methoxide (0.5M, 26.5 ml). The solid was collected, washed with methanol and then ether, and dried to provide 2.51 grams of the free base, melting point 250°–253° C.

$^1$H NMR (TFA): δ 3.10 (singlet, 3H, 1-CH$_3$), δ 4.16 (singlet, 3H, OCH$_3$), δ 4.23 (singlet, 3H, OCH$_3$), δ 7.36 (singlet, 1H, ArH), δ 7.50 (singlet, 1H, ArH).

IR(KBr): 3400, 1650, 1500, 1440, 1255 cm$^{-1}$.

Mass spectrum (DCI): 235 (M+1)+.

Anal. Calculated for C$_{18}$H$_{20}$N$_2$O$_5$: C, 61.52; H, 6.02; N, 11.96. Found: C, 61.41; H, 6.20; N, 11.64.

EXAMPLE 3

4-Acetamido-3-hydroxy-6,7-dimethoxy-1-methylisoquinoline Hemihydrate (Compound BG)

A slurry of 2.028 grams 3-hydroxy-6,7-dimethoxy-1-methyl-4-nitroisoquinoline (BA) (7.67 mmol) in 28 ml acetic anhydride and 180 ml acetic acid was hydrogenated using 0.8 grams of a 10% palladium on carbon catalyst at 25 psi hydrogen pressure in a Parr hydrogenator for 3 hours. The mixture was filtered through a Celite pad, and the collected solids were washed with acetic acid. The filtrate and the wash liquids were combined and evaporated to dryness. The residue was recrystallized from methanol to provide 0.70 grams of Compound BG (33% yield) having a melting point of >300° C. (with decomposition).

$^1$H NMR (TFA): δ 2.63 (singlet, 3H, 4-NHCOCH$_3$); δ 3.12 (singlet, 3H, 1-CH$_3$); δ 4.17 (singlet, 3H, OCH$_3$); δ 4.20 (singlet, 3H, OCH$_3$); δ 7.30 (singlet, 1H, ArH); δ 7.48 (singlet, 1H, ArH); δ 5.28 (broad singlet, 1H, 4-NHCOCH$_3$).

Mass spectrum: m/e 276 (M+).

Anal. Calculated for C$_{14}$H$_{16}$N$_2$O$_4$.½H$_2$O: C, 58.94; H, 6.01; N, 9.82. Found: C, 59.16; H, 5.74; N, 9.85.

EXAMPLE 4

3-Hydroxy-4-isobutyramido-6,7-dimethoxy-1-methylisoquinoline ¼ hydrate (Compound BO)

4-Amino-3-hydroxy-6,7-dimethoxy-1-methylisoquinoline (BBQ) (1.772 grams, 5 mmol) as the diacetate solvate in 50 ml methylene chloride was treated with 2.5 ml triethylamine (16.5 mmol) for 5 minutes and subsequently with 0.63 ml isobutyryl chloride (6 mmol) with stirring under a nitrogen atmosphere. After 1 hour, the slurry was evaporated to dryness in vacuo and boiled in 50 ml methanol and 5 ml water for 15 minutes. The solid was isolated by filtration, washed successively with methanol and acetone, and then dried in vacuo at 50° C. to provide 0.6 grams of Compound BO (39.4% yield) having a melting point of 292°–294° C. (with decomposition).

$^1$H NMR (TFA): δ 1.52 (doublet, J=7 Hz, 6H, CH(CH$_3$)$_2$); δ 3.12 (singlet, 3H, 1-CH$_3$); δ 4.15 (singlet, 3H, OCH$_3$); δ 4.18 (singlet, 3H, OCH$_3$); δ 7.23 (singlet, 1H, ArH); δ 7.50 (singlet, 1H, ArH); δ9.20 (broad singlet, 1H, NH).

Mass spectrum: m/e 304 (M+), 276 (M+-CO), 261 [M+-CH(CH$_3$)$_2$], 234 [M+-COCH(CH$_3$)$_2$].

Anal. Calculated for C$_{16}$H$_{20}$N$_2$O$_4$.¼H$_2$O: C, 62.22; H, 6.66; N, 9.07. Found: C, 61.92; H, 6.53; N, 9.03.

EXAMPLE 5

6,7-Dimethoxy-3-hydroxy-1-methyl-4-ureidoisoquinoline (Compound BM)

4-Amino-3-hydroxy-6,7-dimethoxy-1-methylisoquinoline (BBQ) (1.772 grams, 5 mmol) as the diacetate solvate was dissolved in 50 ml of acetic acid under a nitrogen atmosphere, and 0.39 grams of sodium cyanate (6 mmol) were added in one portion. A clear solution formed which became a thick slurry within 5–10 minutes. The mixture was stirred at room temperature overnight. The solid was collected by filtration, washed successively with acetic acid, ethyl acetate, acetone, and ether, and then dried to provide the monoacetate solvate of Compound BM as a yellow solid. The solid was slurried in 50 ml methanol, treated with 5 ml triethylamine (an excess), and the mixture was refluxed under nitrogen for 1 hour. The slurry was filtered, and the isolated yellow solid was washed with methanol and dried in vacuo at 75° C. overnight to provide 0.80 grams of Compound BM (57.8% yield) having a melting point of 250°–255° C. (with decomposition).

$^1$H NMR (TFA): δ 3.13 (singlet, 3H, 1-CH$_3$); δ 4.18 (singlet, 3H, OCH$_3$); δ 4.22 (singlet, 3H, OCH$_3$); δ 7.42 (singlet, 1H, ArH); δ 7.53 (singlet, 1H, ArH); δ 8.08 (broad singlet, 1H).

Mass spectrum: 277 (M+), 260 (M+-NH$_3$), 245 (M+-NH$_3$-CH$_3$), 234 (M+-NCOH).

Anal. Calculated for C$_{13}$H$_{15}$N$_3$O$_4$: C, 56.31; H, 5.45; N, 15.15. Found: C, 55.94; H, 5.45; N, 14.71.

EXAMPLE 6

4-(N'-n-Butylureido)-3-hydroxy-6,7-dimethoxy-1-methylisoquinoline Hemihydrate (Compound BR)

To a stirred solution of 1.722 grams 4-amino-3-hydroxy-6,7-dimethoxy-1-methylisoquinoline (BBQ) (5 mmol) as the diacetate solvate in 9 ml acetic acid at room temperature were added dropwise 0.68 ml n-butylisocyanate (6 mmol) over a 3 minute period. Within the first 30 minutes, the reaction mixture became a thick gel and was diluted with an additional 2 ml of acetic acid. The viscous slurry was stirred for about 16 hours. The solid was isolated by filtration, washed successively with a small volume of acetic acid, acetone and ether. The solid was dried in vacuo to provide 0.68 grams of Compound BR as a greenish-grey solid (41.3% yield) having a melting point of 230°–232° C. (with decomposition).

$^1$H NMR (TFA): δ 1.02 (triplet, J=7 Hz, 3H, CH$_3$(CH$_2$)$_3$); δ 1.58 (broad multiplet, 4H, CH$_3$(CH$_2$)$_2$); δ 3,10 (singlet, 3H, 1-CH$_3$); δ 4,83 (broad triplet, J=7 Hz, 2H, NHCONHCH$_2$); δ 4.17 (singlet, 3H, OCH$_3$); δ 4.20 (singlet, 3H, OCH$_3$); δ 7.38 (singlet, 1H, ArH); δ 7.50 (singlet, 1H, ArH); δ 8.00 (broad singlet, NH or OH).

Mass spectrum: m/e 333 (M+, weak), 260 (M+-H$_2$N(CH$_2$)$_3$CH$_3$), 234 (BP).

Anal. Calculated for C$_{17}$H$_{23}$N$_3$O$_4$¼H$_2$O: C, 59.62; H, 7.06; N, 12.27. Found: C 59.66; H, 6.80; N, 11.95.

The compounds listed in Table 1 wherein R$_4$ is NHCONHR and R is alkyl, aryl, and substituted aryl radicals thereof are also prepared according to the method of Example 6 using the appropriate isocyanate in acetic acid solvent or in other appropriate solvents such as chloroform or tetrahydrofuran. For example, the following isocyanates can be used in the foregoing method to provide the indicated compounds: para-methoxyphenyl isocyanate (Compounds BF and BT); meta-methoxyphenylisocyanate (Compounds BU and BAE); 3,4,5-trimethoxyphenyl isocyanate (Compounds BAB and BAH); para-trifluoromethylphenyl isocyanate (Compounds BV, BZ and BAD); meta-trifluoromethylphenyl isocyanate (Compounds BY and BAG); and para-hole (and meta-halo) phenyl isocyanates (Compounds BW, BX, BAA, BAC, BAF and BAI).

EXAMPLE 7

4-[N-(n-Butoxycarbonyl)amino]-3-hydroxy-6,7-dimethoxy-1-methylisoquinoline (Compound BBP)

n-Butylchloroformate (0.578 gram, 4.24 mmol) was added to a slurry of amine BBQ (0.900 gram, 3.85 mmol) and triethylamine (0.409 gram, 4.04 mmole) in chloroform (50 mL). The mixture was stirred overnight and the solid was collected by filtration and washed with methanol followed by ether. Trituration of the solid with methanol gave Compound BBP (0.520 gram, 40% yield) of melting point 282°-84° C. (with decomposition).

$^1$H NMR (TFA): δ 0.67–2.3 (m, 7H, OCH$_2$(CH$_2$)$_2$CH$_3$), 3.12 (s, 3H, 1-CH$_3$), 3.90–4.62 (m, 2H, OCH$_2$(CH$_2$)$_2$CH$_3$) overlapping 4.18 (s, 3H, Ar-OCH$_3$), 4.22 (s, 3H, Ar-OCH$_3$), 7.40 (s, 1H, Ar-H), 7.48 (s, 1H, Ar-H), 7.83 (s, 1H, NH).

IR (KBr): 3300, 2970, 1710, 1665, 1500, 1450, 1260 cm$^{-1}$.

Mass Spectrum (DCI): m/e 335 (M+1)$^+$. Anal. Calculated for C$_{17}$H$_{22}$N$_2$O$_5$: C, 61.06; H, 6.63; N, 8.38. Found: C, 60.79; H, 6.84; N, 8.07.

EXAMPLE 8

4-[N-(4-Carboxyphenyl)ureido]-3-hydroxy-6,7-dimethoxy-1-methylisoquinoline.5/2 Hydrate (Compound BCA)

A slurry of Compound BBC (1.00 gram, 2.35 mmol) in aqueous sodium hydroxide (2N; 50 mL) was stirred overnight and then acidified with aqueous hydrochloric acid (3N). The yellow solid was collected by filtration and washed sequentially with acetone, water, and ether. The solid was dried under vacuum to give Compound BCA (0.72 gram, 77% yield) of melting point 244°–246° C. (with decomposition).

$^1$H NMR (TFA): δ 3.28 (s, 3H, 1-CH$_3$), 4.18 (s, 3H, ArOCH$_3$), 4.21 (s, 3H, ArOCH$_3$), 7.32–8.05 (m, 5H, aryl H), 8.15–8.38 (m, 3H, Ar and ureido-NH), 10.5 (br s, 1H, exchangeable proton).

IR (KBr): 3600–2100 (br), 1650, 1540, 1490, 1245 cm$^{-1}$.

Mass Spectrum (FAB): m/e 398 (M+1)$^+$.

Anal. calculated for C$_{20}$H$_{19}$N$_3$O$_6$.5/2H$_2$O: C, 54.29; H, 5.08; N, 9.49. Found: C, 54.69; H, 4,98; N, 9.61

EXAMPLE 9

3-Hydroxy-6,7-dimethoxy-4-[N-(4-methylsulfonylphenyl)ureido]-1-methylisoquinoline ¼ Hydrate (Compound BCB)

To a slurry of Compound BBI (1.00 gram, 2.40 mmol) in acetic acid (50 mL) was added sodium perborate (0.404 gram, 2.62 mmol) and the mixture was stirred at 50° C. for 1.5 hours and then allowed to cool to room temperature. The yellow solid was collected, washed sequentially with water acetone, and ether, and then triturated with methanol to give Compound BCB (0.484 gram, 46.6% yield) of melting point 220°–222° C. (with decomposition).

$^1$H NMR (TFA): δ 3.15 (s, 6H, 1-CH$_3$ and SOCH$_3$), 4.2 (s, 6H, Ar-OCH$_3$×2), 7.43 (br s, 1H, Ar-H), 7.50 (s, 1H, Ar-H), 7.83 (s, 4H, aryl protons), 8.15 (br s, 1H, ureido-NH), 8.67 (br s, 1H, ureido-NH).

IR (KBr): 3140, 1640, 1520, 1485, 1245 cm$^{-1}$.

Mass Spectrum (DCI): m/e 416 (M+1)$^+$.

Anal. Calculated for C$_{20}$H$_{21}$N$_3$O$_5$S.¼H$_2$O: C, 57.19; H, 5.16; N, 10.00; S, 7.63. Found: C, 57.20; H, 5.13; N, 9.61; S, 6.79

RESULTS

A. Cardiotonic Activity

The acute in vivo cardiotonic activity of compounds prepared according to the present invention was determined according to a modification of the procedure described by Alousi et al., Circ. Res., 45, 666 (1979).

In particular, adult mongrel dogs were anesthetized with sodium pentobarbital and were artificially respired. Arterial pressure was monitored via a femoral artery, and the pulse pressure was used to trigger a cardiotachometer for heart rate. Left ventricular pressure was determined with a Millar catheter, and dP/dt (the change in ventricular pressure with time) was derived. Cardiac output was determined by measuring ascending aortic blood flow with an electromagnetic flow probe, and myocardial contractile force was measured with a Walton Brodie strain gauge sutured to the right ventricle. Lead II EKG was also recorded.

A standard dose (10 μ/kg/min) of dopamine was administered to assess myocardial responsiveness.

Compounds of the invention were administered by intravenous infusion or bolus oral administration, and the effects on cardiovascular parameters were determined. The total amount of each compound that was administered is shown in Table 2, hereinafter.

Dose related effects on the test compound on blood pressure (BP), heart rate (HR), maximum change in left ventricular pressure with time (dP/dt max), % change in cardiac force (CF) and the increase in mean arterial blood pressure relative to controls (MABP) were compared to pretreatment control values, expressed as a % change and rated for activity. Statistical evaluations were made using the appropriate parametric test against controls. Data for the isoquinolinols of this invention are summarized in Table 2.

B. Renal Vasodilating Activity

Goldberg et al, J. Pharmacol. Exp. Ther., 163, 188 (1968), performed an investigation of the structural requirements for dopamine-like renal vasodilation of phenethylamines and apmorphine. The following procedure is a variation of the assay described in that report.

Adult mongrel dogs were anesthetized and surgically prepared for electromagnetic measurement of renal artery blood flow. A carotid artery was cannulated for measuring arterial blood pressure, and drugs were administered intravenously or intraarterially (via the renal artery). Heart rate was monitored with a cardiotachometer. Renal vascular resistance was calculated as the ratio of mean arterial blood pressure/renal artery blood flow. Dopamine was infused intravenously at 3 mg/kg/min for ten minutes (at an infusion rate of about 1 ml/min) to determine responsiveness of each dog to renal dopamine receptor stimulation. Cumulative doseresponse data were obtained by infusing a compound of this invention at progressively increasing (usually threefold) infusion rates, esch dose being infused for five minutes. The maximum percent increase from pre-drug control in renal artery blood flow (or a decrease in renal vascular resistance) was determined for each infusion dose.

Representative data for the isoquinolinols of this invention are summarized in Table 2. RBF values are percent increase in renal blood flow. RVR values are percent increase in renal vascular resistance. MABP and HR are increases in mean arterial blood pressure and heart rate, respectively, relative to controls.

increase, and a decrease in mean arterial blood pressure (MABP).

The compounds of this invention also produce an increase in renal blood flow (RBF), a decrease in renal vascular resistance (RVR), a decrease in mean arterial blood pressure (MABP) with only a minimal increase in heart rate (HR)—less than about 30%.

C. Inhibition of Phosphodiesterase Fraction III Activity

Thompson et al. describe a cyclic nucleotide phosphodiesterase assay in *Advances in Cyclic Nucleotide Research,* Brooker et al., eds., 10, 69–92 (1979). The

TABLE 2

Cardiotonic and Renal Vasodilator Activities of Isoquinolinols

| COMPOUND | CARDIOTONIC | | | | | RENAL VASODILATOR | | | |
| --- | --- | --- | --- | --- | --- | --- | --- | --- | --- |
| | DOSE* | CF | dP/dt | HR | MABP | DOSE* | RBF | RVR | MABP | HR |
| | (Controls) | | | | | | | | | |
| BA | 0.150 | 92 | 63 | 8 | −19 | 0.2 | +14 | −23 | −12 | +83 |
| BB | 1.875 | 28 | −1 | −17 | −8 | 6.2 | +19 | −30 | −16 | +90 |
| BC | 1.875 | 16 | 22 | 0 | −7.5 | 1.2 | +20 | −28 | −14 | −6 |
| BE | 0.875 | 84 | 38 | 18 | −22 | 1.2 | +60 | −52 | −26 | +32 |
| BF | 1.875 | 23 | 38 | 7 | 1 | 6.2 | +30 | −12 | +14 | −8 |
| BG | 8.75 | 47 | 33 | 5 | −3 | 6.2 | +39 | −24 | +6 | +14 |
| BH | 0.125 | 134 | 74 | 18 | −24 | 0.04 | +25 | −28 | −10 | +19 |
| BI | 0.375 | 118 | 8 | 30 | −35 | 0.14 | +16 | −18 | −8 | +16 |
| BJ | 1.875 | 21 | 8 | −3 | 1 | 6.34 | +18 | −19 | −4 | −16 |
| BK | 0.375 | 62 | 22 | 11 | −2 | 0.34 | +14 | −30 | −21 | +3 |
| BL | 1.875 | 10 | 11 | −29 | −15 | 0.34 | +13 | −5 | +6 | +29 |
| BM | N.T. | | | | | 6.2 | +59 | −23 | +18 | −10 |
| BP | N.T. | | | | | 6.2 | +68 | −32 | +12 | +2 |
| BR | N.T. | | | | | 6.2 | +128 | −56 | −1 | −9 |
| BS | N.T. | | | | | 6.2 | +33 | −24 | — | +4 |
| BV | N.T. | | | | | 6.2 | +25 | −24 | −6 | +26 |
| BAB | N.T. | | | | | 6.2 | +16 | −22 | −9 | +3 |
| BAD | N.T. | | | | | 6.2 | +49 | −29 | +4 | +10 |
| BAE | N.T. | | | | | 6.2 | +58 | −36 | — | −2 |
| BAF | N.T. | | | | | 6.2 | +30 | −20 | — | +4 |
| BAG | N.T. | | | | | 6.2 | +23 | −16 | +2 | −10 |
| BAJ | N.T. | | | | | 6.2 | +54 | −32 | −11 | −6 |
| BAN | 0.12 | 49 | 12 | 4 | −18 | 6.2 | +61 | −37 | +1 | −5 |
| BAO | N.T. | | | | | 1.2 | +96 | −44 | +8 | −3 |
| BAP | N.T. | | | | | 1.2 | +17 | −26 | −14 | −1 |
| BAR | N.T. | | | | | 1.2 | +9 | −8 | — | — |
| BAU | N.T. | | | | | 6.2 | +12 | −13 | −3 | +4 |
| BAV | N.T. | | | | | 6.2 | +35 | −29 | −5 | +9 |
| BAY | N.T. | | | | | 6.2 | +85 | −35 | +19 | +27 |
| BBA | N.T. | | | | | 6.2 | +53 | −17 | +23 | +2 |
| BBE | N.T. | | | | | 1.2 | +24 | −16 | +3 | +2 |
| BBF | N.T. | | | | | 1.2 | +19 | −24 | −9 | −14 |
| BBG | N.T. | | | | | 1.2 | +15 | −11 | +1 | +12 |
| BBL | N.T. | | | | | 1.2 | +13 | −8 | +5 | −1 |
| BBM | N.T. | | | | | 0.2 | +12 | −10 | — | −1 |
| BBP | N.T. | | | | | 6.2 | +77 | −42 | +1 | — |
| BBQ | 0.875 | 99 | 106 | 7 | −5 | 1.2 | +22 | −12 | +6 | +4 |
| BBR | N.T. | | | | | 6.2 | +30 | −29 | −7 | +27 |
| BBS | N.T. | | | | | 1.2 | +17 | −4 | +2 | +5 |
| BBX | N.T. | | | | | 1.2 | +12 | −20 | −11 | −11 |
| BBY | N.T. | | | | | 1.2 | +21 | −12 | +6 | −4 |
| BBZ | N.T. | | | | | 1.2 | +22 | −12 | +5 | +8 |
| BCA | N.T. | | | | | 1.2 | +40 | −28 | −1 | −12 |
| BCB | N.T. | | | | | 1.2 | +12 | −6 | +5 | −1 |
| BCD | N.T. | | | | | 1.2 | +28 | −22 | — | — |

*Dose: Intravenous, milligrams of compound per kilogram body weight.
N.T. indicates "not tested".
CF is the percent change in cardiac force.
dP/dt is the maximum change left ventricular pressure with time.
HR is the percent change in heart rate.
MABP is the mean arterial blood pressure.
RBF is the renal blood flow.
RVR is the renal vascular resistance.
All values are expressed as percent change relative to controls.

As shown in Table 2, the compounds of this invention produce an increase in cardiac force (CF), an increase in the left ventricular pressure with time (dP/dt), a minimal increase in heart rate (HR)—less than 25 to 30% following procedure is based on that published assay and measures the ability of compounds to inhibit cyclic nucleotide phosphodiesterase which is an enzyme that converts either cyclic AMP or cyclic GMP to the non-cyclized AMP or GMP, respectively.

Compounds were tested at various concentrations in the presence of cyclic AMP (0.10–1.0 uM containing 0.2 microCuries $^3$H-cyclic AMP), cyclic nucleotide phosphodiesterase, and 0.05M Tris-Cl buffer (pH 7.4, containing 5 mM magnesium chloride). After a specified time, the reaction was stopped by heating to 100° C. for 1 minute. After cooling, 0.10 ml of a solution containing snake venom (1 mg/ml) was added, and the reaction was allowed to proceed for 30 min. Termination of this reaction was accomplished by the addition of 1.0 ml of 33% DOWEX AG1X8 resin slurry (Dow Chemical Co., Midland, MI) to separate the product from the unconverted substrate. An aliquot was removed from the supernatant and analyzed by liquid scintillation spectrometry.

The fraction III enzyme was isolated as an isozyme from the crude canine heart homogenate by ion exchange chromatography. The enzyme activity was designated fraction III since it is the third and last phosphodiesterase activity to be eluted from the chromatographic column. The fraction III enzyme has a relatively high affinity and specificity for the cyclic AMP.

Data are presented as the $IC_{50}$ which is the concentration (in micromoles) of a compound that was required to inhibit 50% of the cyclic nucleotide phosphodiesterase activity.

Data for the isoquinolinols of this invention are summarized in Table 3.

TABLE 3

| Inhibition of Phosphodiesterase Activity by Isoquinolinols | |
|---|---|
| Compound | Phosphodiesterase fraction III Inhibition ($IC_{50}$ in $\mu$M) |
| BA | 13.0 |
| BC | 142 |
| BF | 410 |
| BG | 250 |
| BH | 8 |
| BI | 2.6 |

As demonstrated by the combination of the foregoing results, the compounds of this invention which are identified in Table 1 herein each exhibit one or more of the following properties: cardiotonic properties, renal vasodilating properties and phosphodiesterase fraction III inhibiting properties.

Moreover, BP—[4-(N'-para-methoxyphenylureido)-3-hydroxy-6,7-dimethoxy-1-methylisoquinoline], BR—[4-(N'-n-butylureido)-3-hydroxy-6,7-dimethoxy-1-methylisoquinoline] and BAO—[4-(N'-allylureido)-3-hydroxy-6,7-dimethoxy-1-methylisoquinoline] are compounds that are particularly preferred according to this invention for use in stimulating vasodilation.

PREPARATION OF STARTNG MATERIALS

Example 1

7-Ethoxy-3-hydroxy-6-methoxy-1-methylisoquinoline

The preparation of the title compound involved two steps as follows, starting with 4-ethoxy-3-methoxyphenylacetonitrile.

A.
3-Acetamido-7-ethoxy-6-methoxy-1-methyl-2-benzopyrylium Perchlorate

To an ice-cooled and stirred soluton of 25 grams 4-ethoxy-3-methoxyphenylacetonitrile (0.13 mmol) in 74 ml acetic ahnydride (0.785 mol) was slowly added perchloric acid (70%, 11.7N, 15.5 ml, 0.182 mol) over a 15 minute period. The dark reaction mixture slowly became a yellow slurry and was stirred at room temperature for 42 hours. The mixture was diluted with 200 ml diethyl ether and a crystalline yellow solid was isolated by filtration, washed with diethyl ether and dried in vacuo to provide 47.3 grams of product (100% yield) having a melting point of 188°–189° C. (with decomposition).

B. To an ice-cooled slurry of 36.37 grams of 3-acetamido-7-ethoxy-6-methoxy-1-methyl-2-benzopyrylium perchlorate (0.1 mol) in water (400 ml) was slowly added 80 ml of concentrated ammonium hydroxide over a 10 minute period. The mixture was stirred for additional 30 minutes. The light yellow precipitate that formed was filtered, washed with water and dried to provide 23 grams of the crude title 3-isoquinolinol (100%). Recrystallization from methanol/chloroform mixture (2000 ml:700 ml) provided 18.7 grams (81.3%) of pure title 3-isoquinolinol having a melting point of 235°–240° C.(d).

Anal. Calculated for $C_{13}H_{15}NO_3 \cdot \frac{1}{4}H_2O$: C, 65.66; H, 6.57; N, 5.89. Found: C, 65.96; H, 6.43; N, 6.14

Using the appropriately substituted phenylacetonitrile or phenylacetic ester in the above procedure, the various 3-isoquinolinol compounds were obtained using the intermediacy of the corresponding benzopyrylium perchlorates.

Example 2

3-Hydroxy-7,8-dimethoxy-1-methylisoquinoline (Compound C)

Polyphosphoric acid was freshly prepared by adding 130 ml phosphoric acid (an 87% aqueous solution) to phosphorus pentoxide. The mixture reacted exothermically and reached a temperature of 100° C. The mixture was rapidly stirred and was maintained at about 100° C. with an oil bath for about 4 hours until all the phosphorous pentoxide dissolved. To this colorless, viscous liquid heated to 93° C. were added 9.62 (30.9 mmol) N-[1-(2,3-dimethoxyphenyl)ethyl]diethoxyacetamide (VI), and the resulting deep red solution was maintained with stirring at 88°–98° C. for 1.5 hours. The reaction mixture was cooled to room temperature and maintained at that temperature overnight. The mixture was then poured into 500 ml ice-water, and the pH were adjusted to 6.8 by adding solid potassium hydroxide. The yellow precipitate that formed was filtered, washed with water and dried to provide 6 grams of the solid. The filtrate was extracted five times with 300 ml chloroform per extraction. The organic layer was dried over sodium sulfate, filtered and evaporated to dryness in vacuo to provide an additional 0.8 grams of the yellow precipitate. The two portions of the yellow precipitate were combined to provide 6.8 grams of material which was chromatographed on a silica gel column (280 grams, 20 mm ID). Elution with a 93:7 methylene chloride:methanol mixture provided 1.4 grams of Compound C (21% yield) which was further purified by recrystallization from ethyl acetate to provide 0.770 grams pure Compound C (11.3% yield) having a melting point of 165° to 166° C.

$^1$H NMR (TFA): δ 3.40 (singlet, 3H, 1-C$\underline{H}_3$); δ 4.15 (singlet, 3H, OC$\underline{H}_3$); δ 4.20 (singlet, 3H, OC$\underline{H}_3$); δ 7.38 (singlet, 1H, 4-$\underline{H}$); δ 7.68 (doublet, J=9 Hz, 1H, Ar$\underline{H}$); δ 7.97 (doublet, J=9 Hz, 1H, Ar$\underline{H}$).

IR (KBr): 6.06μ.

Mass spectrum: m/e 219 (M$^+$).

Anal. Calculated for $C_{12}H_{13}NO_3$: C, 65.74; H, 5.98; N, 6.39. Found: C, 65.42; H, 6.09; N, 6.23.

The present invention has been described with reference to several preferred embodiments. It will be understood, however, that numerous modifications and variations of the disclosed subject matter can be made without departing from the scope of the invention described herein.

What is claimed is:

1. A compound having a structure that corresponds to the formula:

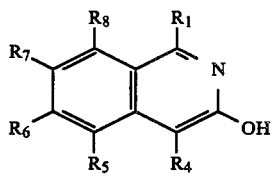

wherein
- $R_1$ is a radical selected from the group consisting of hydrogen, lower alkyl, phenyl, naphthyl, halo lower alkyl, halo phenyl and halo naphthyl wherein the halogen is selected from chloro, bromo, iodo and fluoro;
- $R_4$ is a radical selected from the group consisting of nitro, nitroso, amino, disubstituted amino wherein the substituent is a lower alkyl group having 1–5 carbon atoms, and radicals of the formula NHCO-$(Y)(R)_n$ wherein Y is O or $N(H)_x$ wherein x and n are independently zero, 1 or 2 and R is hydrogen, lower alkyl, cycloalkyl having 3–6 carbon atoms, phenyl, naphthyl, lower alkyl phenyl, lower alkyl naphthyl and substituted phenyl, naphthyl, lower alkyl phenyl and lower alkyl naphthyl wherein the substituent is selected from hydroxy, lower alkoxy, lower alkylthio, halogen, halo lower alkyl, CN, $NO_2$, $SO_2H$ and COZ wherein Z is OR or NR'R'' wherein R' is hydrogen or lower alkyl and R and R'' are hydrogen, lower alkyl, aminolower alkyl, lower alkylaminolower alkyl and lower dialkylaminolower alkyl alkynyl having 3–5 carbon atoms or lower alkoxy; with the proviso that if Y is oxygen R is other than hydrogen and n is 1; and when n is 2, x is zero; and
- $R_5$, $R_6$, $R_7$ and $R_8$ are independently selected from the group consisting of hydrogen, halogen, hydroxy, and lower alkoxy; and $R_5$ and $R_6$, $R_6$ and $R_7$ or $R_7$ and $R_8$ when taken together each form O—CH$_2$—O; and the pharmaceutically acceptable salts thereof.

2. The compound according to claim 1 wherein $R_1$ is lower alkyl or halogen-substituted lower alkyl, $R_4$ is nitro or a radical of the formula NHCO(NH)$_x$R wherein x is zero or 1 and R is selected from hydrogen, lower alkyl, cycloalkyl having 3–6 carbon atoms, phenyl, naphthyl, lower alkyl phenyl, lower alkyl naphthyl and substituted phenyl, naphthyl, lower alkyl phenyl and lower alkyl naphthyl wherein the substituent is selected from hydroxy, lower alkoxy, lower alkylthio, halogen, halo lower alkyl, CN, $NO_2$, $SO_2H$ and COZ wherein Z is OR or NR'R'' wherein R' is hydrogen or lower alkyl and R; and R'' are hydrogen, lower alkyl, aminolower alkyl, lower alkylaminolower alkyl and lower dialkyl-aminolower alkyl and $R_5$ is hydrogen or lower alkoxy, $R_6$ and $R_7$ are each lower alkoxy and $R_8$ is hydrogen or methoxy.

3. The compound according to claim 1 wherein $R_1$ is methyl, $R_4$ is nitro or NHCONHR and R is lower alkyl, phenyl or naphthyl, $R_5$ is hydrogen, $R_6$ and $R_7$ are methoxy or ethoxy and $R_8$ is hydrogen.

4. The compound according to claim 1 which is 3-hydroxy-6-methoxy-7-ethoxy-1-methyl-4-nitroisoquinoline.

5. The compound according to claim 1 which is 3-hydroxy-6-methoxy-7-n-butoxy-1-methyl-4-nitroisoquinoline.

6. The compound according to claim 1 which is 4-(N'-para-methoxyphenyureido)-3-hydroxy-6,7-dimethoxy-1-methylisoquinoline.

7. The compound according to claim 1 which is 4-(N'-n-butylureido)-3-hydroxy-6,7-dimethoxy-1-methylisoquinoline.

8. The compound according to claim 1 which is 4-(N'-allylureido)-3-hydroxy-6,7-dimethoxy-1-methylisoquinoline.

9. The compound according to claim 1 which is 4-(N'-para-carboxyphenylureido)-3-hydroxy-6,7-dimethoxymethylisoquinoline.

10. A pharmaceutical composition comprising an effective amount of a compound according to claim 1 as the active ingredient dispersed in a pharmaceutically acceptable carrier.

11. The pharmaceutical composition according to claim 10 wherein said compound is capable of increasing the efficiency of cardiac contractions in the amount present in the composition when said composition is introduced into a mammal.

12. The pharmaceutical composition according to claim 10 wherein said compound is capable of increasing the contractile force of cardiac muscle in the amount present in the composition when said composition is introduced into a mammal.

13. The pharmaceutical composition according to claim 10 wherein said compound is capable of stimulating renal vasodilation in the amount present in the composition when said composition is introduced into a mammal.

14. The pharmaceutical composition according to claim 10 wherein said compound is capable of inhibiting the hydrolytic activity of phosphodiesterase fraction III in the amount present in the composition when said composition is introduced into a mammal.

15. A method for increasing the contractile force of cardiac muscle in a mammal comprising administering to said mammal a unit dose of the pharmaceutical composition according to claim 10.

16. A method for stimulating vasodilation in a mammal comprising administering to said mammal a unit dose of the pharmaceutical composition according to claim 10.

* * * * *